(12) United States Patent
Gilmore et al.

(10) Patent No.: US 10,168,310 B2
(45) Date of Patent: Jan. 1, 2019

(54) SYSTEM AND METHOD FOR FLUORESCENCE AND ABSORBANCE ANALYSIS

(71) Applicant: Horiba Instruments Incorporated, Irvine, CA (US)

(72) Inventors: Adam Matthew Gilmore, Flemington, NJ (US); Xiaomei May Tong, Edison, NJ (US)

(73) Assignee: HORIBA INSTRUMENTS INCORPORATED, Irvine, CA (US)

( * ) Notice: Subject to any disclaimer, the term of this patent is extended or adjusted under 35 U.S.C. 154(b) by 412 days.

(21) Appl. No.: 14/556,976

(22) Filed: Dec. 1, 2014

(65) Prior Publication Data

US 2015/0083903 A1 Mar. 26, 2015

Related U.S. Application Data

(63) Continuation of application No. 13/042,920, filed on Mar. 8, 2011, now Pat. No. 8,901,513.

(51) Int. Cl.
*G01J 3/02* (2006.01)
*G01N 33/18* (2006.01)
(Continued)

(52) U.S. Cl.
CPC .............. *G01N 33/18* (2013.01); *G01J 3/021* (2013.01); *G01J 3/0294* (2013.01); *G01J 3/12* (2013.01);
(Continued)

(58) Field of Classification Search
CPC ......... G01N 21/645; G01N 2021/6491; G01N 2021/6417
See application file for complete search history.

(56) References Cited

U.S. PATENT DOCUMENTS 3,666,362 A 5/1972 Chance
4,279,511 A 7/1981 Maute et al.
(Continued)

FOREIGN PATENT DOCUMENTS

CN 1360206 A 7/2002
CN 101706434 A 5/2010
(Continued)

OTHER PUBLICATIONS

Principles of Fluorescence Spectroscopy, ISBN No. 978-0-387-31278-1, p. 27-200, (2006) to J.R. Lakowicz (hereinafter "Lakowicz").*
(Continued)

*Primary Examiner* — Kenneth J Malkowski
(74) *Attorney, Agent, or Firm* — Brooks Kushman P.C.

(57) ABSTRACT

A system or method for analyzing a sample include an input light source, an excitation light source positioned to receive light from the input light source and to sequentially illuminate the sample with each of a plurality of wavelengths, a fluorescence detector positioned to receive and substantially simultaneously detect multiple wavelengths of light emitted by the sample for each of the plurality of excitation wavelengths, an absorption detector positioned to receive and detect light passing through the sample, and a computer in communication with the excitation light source, the fluorescence detector, and the absorption detector, the computer controlling the excitation light source to sequentially illuminate the sample with each of the plurality of wavelengths while measuring absorption and fluorescence of the sample based on signals received from the fluorescence and absorption detectors.

17 Claims, 12 Drawing Sheets

(51) Int. Cl.
| | |
|---|---|
| *G01N 21/64* | (2006.01) |
| *G01J 3/12* | (2006.01) |
| *G01J 3/18* | (2006.01) |
| *G01J 3/42* | (2006.01) |
| *G01J 3/44* | (2006.01) |
| *G01N 21/33* | (2006.01) |
| *G01N 21/17* | (2006.01) |

(52) U.S. Cl.
CPC . *G01J 3/18* (2013.01); *G01J 3/42* (2013.01); *G01J 3/4406* (2013.01); *G01N 21/33* (2013.01); *G01N 21/645* (2013.01); *G01N 2021/1734* (2013.01); *G01N 2021/6417* (2013.01); *G01N 2021/6421* (2013.01); *G01N 2021/6491* (2013.01); *G01N 2201/061* (2013.01); *G01N 2201/127* (2013.01)

(56) References Cited

U.S. PATENT DOCUMENTS

| | | | |
|---|---|---|---|
| 4,305,660 | A | 12/1981 | Kallet |
| 4,475,813 | A | 10/1984 | Munk |
| 4,927,265 | A | 5/1990 | Brownlee |
| 5,285,254 | A | 2/1994 | De Sa |
| 5,414,508 | A | 5/1995 | Takahashi et al. |
| 6,236,456 | B1 | 5/2001 | Giebeler et al. |
| 6,970,241 | B1 | 11/2005 | DeSa |
| 7,209,223 | B1 | 4/2007 | Hull et al. |
| 7,265,827 | B2 | 9/2007 | Slutter et al. |
| 7,324,202 | B2 | 1/2008 | Leonard et al. |
| 7,569,839 | B2 | 8/2009 | Gilmore et al. |
| 7,595,881 | B2 | 9/2009 | Leonard et al. |
| 2005/0057753 | A1 | 3/2005 | Mosley et al. |
| 2005/0264803 | A1 | 12/2005 | Jones |
| 2007/0037135 | A1 | 2/2007 | Barnes et al. |
| 2008/0174767 | A1 | 7/2008 | Leonard et al. |
| 2008/0192249 | A1 | 8/2008 | Babichenko et al. |
| 2008/0272312 | A1 | 11/2008 | Tuschel |
| 2010/0308234 | A1 | 12/2010 | Harju et al. |
| 2011/0186753 | A1* | 8/2011 | Dixon .............. G01N 21/64 250/459.1 |

FOREIGN PATENT DOCUMENTS

| | | |
|---|---|---|
| EP | 0674160 A1 | 9/1995 |
| EP | 0616211 B1 | 1/1999 |
| JP | 2005331419 A | 12/2005 |
| JP | 2009505070 A | 2/2009 |
| WO | 0063680 A1 | 10/2000 |
| WO | 2007019462 A2 | 2/2007 |

OTHER PUBLICATIONS

Chinese Office Action for Chinese Application No. 201280017574.9 dated Mar. 18, 2015.

Kling. "Fluorometers Dissected, Fluorometry offers lower detection limits for various applications", Analytical Chemistry Mar. 1, 2000, p. 219A-224A.

Holland et al. "A Unique Computer Centered Instrument for Simultaneous Absorbance and Fluorescence Measurements", Analytical Chemistry Jan. 1973, vol. 45, No. 1, p. 145-153.

Monte et al. "Minimizing Uncertainty for Traceable Fluorescence Measurements-The BAM Reference Fluorometer", Federal Institute for Materials Research and Testing (BAM) Working Group Optical Spectroscopy, I.3, Richard-Willstatter-Strabe 11, D-12489 Berlin, Germany. 2005, 1 Page.

"PHAR 7633 CHapter 24, Pharmaceutical Analysis, Drug Quantitation", http:www.boomer.org/c/p4/c24-c2403.html, Retrieved Dec. 9, 2010, 8 Pages.

"Fluorescence spectroscopy—Wikipedia, the free encyclopedia", http://en.wikipedia.org/wiki/Fluorescence_spectroscopy, Retrieved Dec. 9, 2010, 5 Pages.

"STAR Grant R832738: Rapid Detection of Trace Endocrine Disrupting Chemicals in Complex Mixtures: A Full-Spectrum Deconvolution Technique with a UV-Transparent Passive Concentrator", http://www.epa.gov/ppcp/project/star-grant1.html, Retrieved Aug. 6, 2010, 2 Pages.

J.R. Lakowicz; "Principles of Fluorescence Spectroscopy," ISBN No. 978-0-387-31278-1, p. 27-61, 2006.

Chen et al., "Light Source Compensation in Absorption and Transmission Spectral Measurements," Acton Research Corporation, p. 1-3, 1998.

McPherson, "Additive or Subtractive Mode Double Monochromator," 2006, p. 1-2, available at http://www.mcphersoninc.com/spectrometers/uvvisir/model275d.htm.

International Search Report for PCT/US2012/027833, dated May 30, 2012.

International Preliminary Report on Patentability dated Sep. 10, 2013, for corresponding PCT Application PCT/US2012/027833 filed Mar. 6, 2012.

Extended European Search Report for European Patent Application No. 12754324.7 dated Aug. 21, 2014.

Japanese Office Action for Japanese Application No. 2013-557795 dated Jan. 5, 2016.

European Examination Report for European Application No. 12754324.7 dated May 24, 2017.

Examination Report for Indian Patent Application No. 8066/CHENP/2013 dated Feb. 27, 2018.

\* cited by examiner

SYSTEM AND METHOD FOR FLUORESCENCE AND ABSORBANCE ANALYSIS

CROSS-REFERENCE TO RELATED APPLICATION

This application is a continuation of U.S. application Ser. No. 13/042,920 filed Mar. 8, 2011, the disclosure of which is hereby incorporated by reference in its entirety.

TECHNICAL FIELD

The present disclosure generally relates to quantitative and/or qualitative analysis of a sample using fluorescence and absorbance measurements.

BACKGROUND

Spectroscopic analysis, including absorption spectroscopy and fluorescence spectroscopy, may be used to identify and measure or quantitate various types of suspended and dissolved organic and/or inorganic materials or compounds present within a sample. These types of analyses have a wide variety of applications in chemistry, food science, biology, pharmacology, materials/nanotechnology, and water quality analysis in various environmental, geology, hydrology, oceanography/limnology, and soil science applications, for example. Spectrophotometric measurements may be used to detect and quantitate compounds that include chromophores that absorb light in the visible-ultraviolet (VIS-UV) range having wavelengths of between about 700-200 nm, respectively, for example. The amount of light energy absorbed generally varies with the concentration of the compound and the distance traveled through the compound. Likewise, some compounds can be identified and quantitated based on characteristic fluorescence associated with colored or chromophoric matter, i.e. absorption of shorter wavelength excitation light energy and re-emission of longer wavelength (and lower energy) emission light energy.

Absorption and fluorescence spectroscopy have been used in water quality analysis applications to identify and measure colored or chromophoric dissolved organic matter (CDOM), which may include various types of compounds, such as humic and fulvic acids, chlorophylls, proteins and amino acids, nucleic acids, sewerage, bacteria, fertilizers, pesticides, etc. One prior art strategy is to perform separate fluorescence and absorbance measurements using corresponding instruments. The resulting data may be correlated and/or corrected using various commercially available software applications. However, separate measurements require transfer of the sample and data for desired analyses and fluorescence spectral corrections. In addition, fluorometers that use scanning excitation and emission monochromators having single channel detectors (typically photomultiplier tubes (PMT's)) often have scanning times of 30-90 minutes or more and may not accurately detect and quantitate unstable compounds that can degrade over time and/or with exposure to the excitation light. Similarly, the accuracy of results obtained using such long scanning times may be adversely affected by time-dependent changes in dissolved gases, pH, aggregation, sedimentation, and other chemical processes. Long scanning times combined with relatively limited Raman signal-to-noise ratios may provide uncertainty and statistical inaccuracy of the coordinated absorbance and fluorescence readings.

To address some of the above issues, commercially available fluorescence instruments have been developed to facilitate parallel fluorescence and absorbance readings. However, even this approach does not provide near simultaneous collection of absorbance and emission data for fluorescence reabsorbance correction. In addition, general purpose instruments may have various design compromises to accommodate both absorbance and fluorescence measurements.

SUMMARY

A system or method for analyzing a sample include an input light source, a double subtractive monochromator positioned to receive light from the input light source and to sequentially illuminate the sample with each of a plurality of wavelengths, a multi-channel fluorescence detector positioned to receive and detect multiple wavelengths of light emitted by the sample for each of the plurality of excitation wavelengths, an absorption detector positioned to receive and detect light passing through the sample, and a computer in communication with the monochromator, the fluorescence detector, and the absorption detector, the computer controlling the monochromator to sequentially illuminate the sample with each of the plurality of wavelengths while measuring absorption and fluorescence of the sample based on signals received from the fluorescence and absorption detectors.

Various embodiments according to the present disclosure include a method for analyzing a sample that includes illuminating the sample at a plurality of excitation wavelengths from a double subtractive monochromator, measuring absorbance of the sample by detecting light passing through the sample and fluorescence of the sample by detecting an emission spectrum of light emitted by the sample for each excitation wavelength using a multi-channel detector; and correcting the fluorescence measurement using the absorbance measurement. The method may also include adjusting at least one of the absorbance and fluorescence measurements based on light intensity detected by a reference detector positioned to receive a portion of excitation light from the monochromator.

In one embodiment, a system for analyzing a water sample includes a monochromated excitation source having an input implemented by a UV-enhanced Xenon lamp. The light from the lamp passes through a double grating monochromator having two concave holographic gratings arranged in a subtractive configuration to provide near zero dispersion and reduce stray light of non-selected wavelengths while maintaining accurate wavelength tracking. Lamp output is measured/monitored by a reference diode at each wavelength increment of the excitation scan and can be used to correct or normalize the absorption and/or fluorescence measurements. The excitation beam steering for the fluorescence measurements uses fast optics with a numerical aperture selected for increased throughput. A photodiode, diode array, or spectrometer may be included to provide absorption measurements based on substantially collimated light from the excitation beam that passes through the sample and an aperture with the absorbance detector optics having an F/number less than the excitation optics, i.e. in one embodiment, the excitation optics may be characterized by an F/number of about F/3 while the absorbance detector optics may be characterized by an F/number of about F/11. The collimated light associated with the slower optics enhances accuracy and linearity of absorbance readings. Light associated with fluorescence or luminescence of the sample is directed by associated fast optics positioned generally perpendicular to the excitation beam to a spectrograph having a cooled multichannel detector, such as a CCD detector, to facilitate rapid spectra collection with low dark noise. The F/number associated with the fluorescence detector optics may be less than the absorbance detector optics. In one embodiment, the fluorescence detector optics has an F/number of about F/3. A computer and/or controller may collect a complete emission spectrum, which is normalized by the excitation beam intensity measured by the reference photodiode, with corresponding absorption data based on light from the single/common illumination source transmitted through the sample.

Systems and methods according to various embodiments of the present disclosure provide a number of advantages in addition to those described above. For example, various embodiments according to the present disclosure facilitate qualitative and quantitative analysis of dissolved and/or suspended organic and inorganic substances in water samples with desired speed, accuracy, and precision. Instruments and methods according to the present disclosure perform both rapid, simultaneous acquisition of instrument corrected fluorescence excitation-emission spectral maps (EEMs) and absorbance spectra. Various embodiments may include a dedicated and coordinated acquisition and analysis software package to facilitate absorbance and fluorescence measurement analysis. Acquisition of absorbance and fluorescence data in a single instrument reduces or eliminates inaccurate correlations associated with time-dependent optical and chemical changes in the samples between measurements performed by different instruments. Furthermore, substantially simultaneously acquired absorbance data can be used to correlate and correct fluorescence spectral information, in addition to providing a wealth of independent data on dissolved and suspended organic and inorganic compounds. Automatic filtering of the excitation and emission beams as provided by embodiments according to the present disclosure eliminates grating order artifacts.

Various embodiments may be used to generate a fully corrected, three-dimensional spectrum of the fluorescence excitation wavelength, emission wavelength, and intensity spectra in addition to a plot of the transmitted light spectrum. Embodiments may be operated by comparing corresponding blank and unknown samples and applying subsequent processing between the fluorescence EEMs and transmitted light spectra to provide corrected EEM and absorbance/transmittance spectral information. The EEM data can be further analyzed using various known techniques including various types of multivariate analysis, principal component analysis, parallel factors analysis, and/or double-convolution integral methods, for example, to identify and/or quantify sample components associated with the absorption/fluorescence measurements.

Various design strategies, such as use of fast optics for fluorescence measurements using a multi-channel detector and slower optics to provide collimated light to a single channel absorption detector and excitation scanning from longer to shorter wavelengths, for example, reduce required measurement time to eliminate photo-induced changes or damage to sample material to improve quantitative analysis. Similarly, identification of individual spectral components facilitates use of spectral libraries for multivariate analysis techniques. Measurement of absorption and fluorescence in the same instrument using a common excitation source facilitates correction of fluorescence spectra for inner filter effects.

The above advantages and other advantages and features of the present disclosure will be readily apparent from the following detailed description of the preferred embodiments when taken in connection with the accompanying drawings.

DETAILED DESCRIPTION

Various representative embodiments of systems and methods according to the present disclosure are described in detail. However, it is to be understood that the representative embodiments are merely exemplary and systems and methods according to the present disclosure may be embodied in various and alternative forms. The figures are not necessarily to scale and some features may be exaggerated or minimized to show details of particular components. Therefore, specific structural and functional details disclosed herein are not to be interpreted as limiting, but merely as a representative basis for teaching one of ordinary skill in the art to variously employ the present invention.

As those of ordinary skill in the art will understand, various features of the present disclosure as illustrated and described with reference to any one of the Figures may be combined with features illustrated in one or more other Figures to produce embodiments of the present disclosure that are not explicitly illustrated or described. The combinations of features illustrated provide representative embodiments for typical applications. However, various combinations and modifications of the features consistent with the teachings of the present disclosure may be desired for particular applications or implementations.

Figure 1:
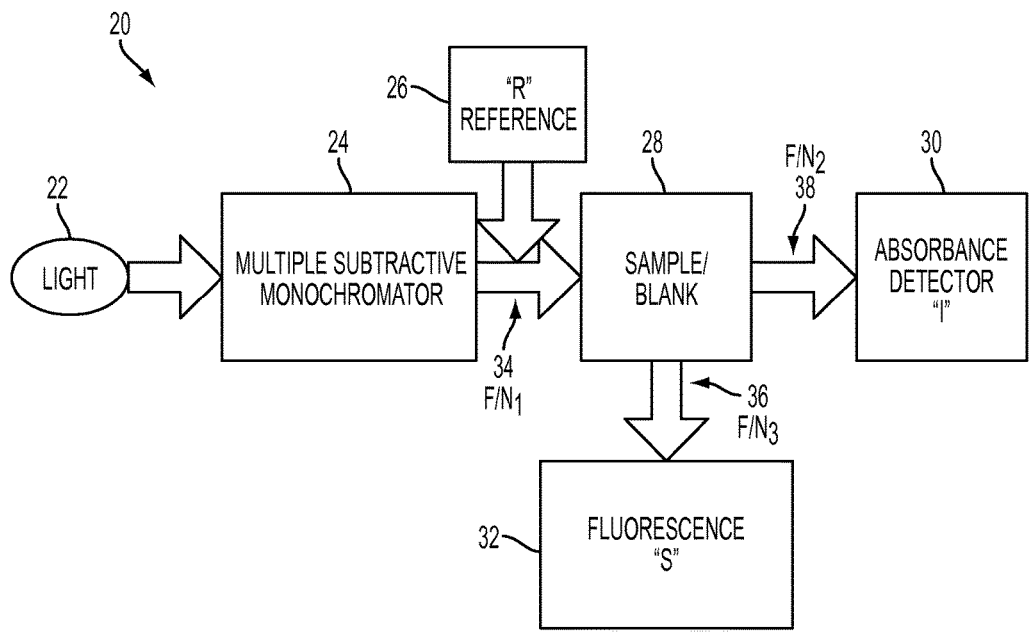
FIG. 1 is a simplified block diagram illustrating functional relationships of core elements in a system or method for analyzing a sample according to embodiments of the present disclosure.

A simplified block diagram illustrating functional relationships among various components of a system or method for analyzing a sample is shown in FIG. 1. System 20 includes an input light source 22 that provides a broad spectrum input light having wavelengths of between about 240-2500 nm, for example. In one embodiment, input light source 22 is implemented by a 150 W UV-enhanced ozone free xenon arc lamp. Of course, selection of an input light source will generally vary by application and implementation. Input light source 22 may include associated optics to generally direct light to the input of an excitation monochromator 24 to improve the system energy efficiency. Excitation monochromator 24 is implemented by a double subtractive monochromator in various embodiments according to the present disclosure. Use of a double subtractive monochromator as the excitation source according to the present disclosure provides near zero dispersion, enhances wavelength tracking accuracy, and reduces stray light of non-selected wavelengths to increase sensitivity of the instrument relative to various prior art strategies. Double subtractive monochromator 24 is positioned to receive light from input light source 22 and to sequentially illuminate a sample and/or blank 28 with each of a plurality of wavelengths. As known by those of ordinary skill in the art, monochromators such as monochromator 24 may be controlled to select a narrow wavelength band from a broad spectrum input light source 22 to provide a narrow band or substantially monochromatic output. For example, in one embodiment, a double subtractive monochromator 24 provides an excitation bandpass or bandwidth of selected wavelengths of about 5 nm and is controlled to scan from a starting wavelength of about 1100 nm to an ending wavelength of about 220 nm in designated increments, such as 1 nm. Because absorption of UV radiation may "bleach" CDOM within a sample reducing its optical density and absorptive capacity, it is desirable to limit the exposure to shorter wavelength light from stray light or prolonged measurement cycles. To reduce bleaching or photo-induced reactions within the sample, excitation scans may proceed from longer wavelengths to shorter wavelengths according to various embodiments of the present disclosure.

Lamp output from source 22 is measured/monitored by a reference detector 26 implemented by a silicon photodiode in one embodiment. Measurements at each wavelength increment of the excitation scan of monochromator 24 may be used to correct or normalize the absorption and/or fluorescence measurements of an absorbance or absorption detector 30 and multichannel fluorescence detector 32. As shown in the Figures, excitation light exiting monochromator 24 is directed through sample and/or blank 28 using associated optics 34 that may be characterized by an associated numerical aperture or F/number generally represented by F/N1. Light passing generally directly through sample and/or blank 28 is directed to absorbance or absorption detector 30 by at least one optical element 38 that may be characterized by a numerical aperture or F/number generally represented by F/N2. Light emitted generally perpendicular or normal to the excitation light from monochromator 24 is directed to multi-channel fluorescence detector 32 by associated optics 36 that may be characterized by an associated numerical aperture or F/number similar or identical to optics 34 as generally represented by F/N3. In various embodiments, fast optics are used to direct light to sample/blank 28 and fluorescence detector 32 with slower optics used to provide substantially collimated light to absorbance detector 30 such that N2 is greater than N1. For example, in one embodiment, optics 34, 36 are fast optics characterized by an F/number of F/3 and positioned to direct light from monochromator 24 and sample 28 with high throughput to fluorescence detector 32 while optics 38 include at least one optical element to direct light from sample/blank 28 and provide a substantially collimated beam to absorption detector 30 characterized by an F/number of F/11. As such, in this embodiment, N1=N3<N2. However, as described in greater detail herein, various embodiments may have F/numbers with N2>N1 and N1>=N3. In general, selecting and positioning optical components to provide absorbance optics characterized by an F/number greater than (or slower than) the F/number of the excitation optics improves linearity and accuracy of absorbance detection. Likewise, selecting and positioning optical components to provide absorbance optics characterized by an F/number greater than the F/number of the fluorescence optics provides more sensitive fluorescence detection with higher throughput in the fluorescence signal.

Multi-channel fluorescence detector 32 is positioned to receive and detect multiple wavelengths of light emitted by sample and/or blank 28 for each of the plurality of excitation wavelengths (or wavelength bands) selected by monochromator 24. Use of a multi-channel detector 32 to simultaneously detect multiple wavelengths of light decreases data collection time that would otherwise be associated with use of a single channel scanning detector. Reduced scanning times also reduce exposure time to excitation wavelengths that may otherwise result in photo-induced changes of the sample. Of course, a single channel scanning detector could be used depending upon the particular application and implementation.

Figure 2:
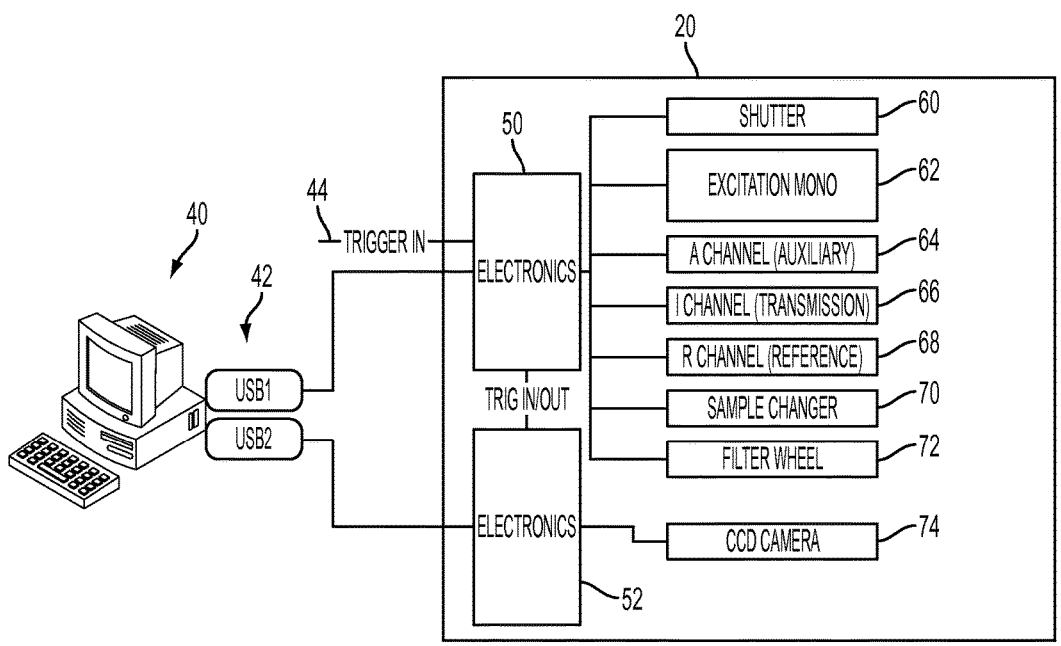
FIG. 2 is a simplified block diagram illustrating functional communication of control and data signals in a system or method for analyzing a sample according to embodiments of the present disclosure.

As also illustrated in FIG. 1, reference detector 26, absorbance detector 30, and fluorescence detector 32 may provide signals on associated data channels to one or more computers or processors as illustrated in FIG. 2. In one embodiment, reference detector 26 provides a data signal "R", absorbance detector 30 provides a data signal "I", and fluorescence detector 32 provides a data signal "S" on corresponding data channels to a central processor or computer.

FIG. 2 is a block diagram illustrating functional connections of various components in a system for analyzing a sample according to embodiments of the present disclosure. Components 20 are coupled to at least one processor or computer 40 via one or more ports 42. In one embodiment, computer 40 includes data processing, analysis, and control software that communicates with various components 20 via USB ports 42 and electronic circuitry/hardware 50, 52. Electronics 50, 52 may provide various signal filtering, processing, conditioning, formatting, etc. to convert signals to/from associated actuators/sensors for communication with computer 40 via ports 42. In one embodiment, an external trigger signal 44 may also be provided to electronics 50 to initiate various instrument functions. Similarly, a trigger input/output signal may be communicated between electronics 50, 52 to coordinate control of various instrument components 20.

As shown in FIG. 2, control logic implemented by software and/or hardware on computer 50 may be used to send/receive corresponding data/control signals via I/O port 42 and electronics 50 for shutter 60, excitation monochromator 62, detector data channels 64, 66, 68, sample changer 70, and filter wheel 72, for example. Similarly, a second I/O port 42 may be used to communicate corresponding data/control signals via electronics 52 to CCD camera 74 associated with a fluorescence spectrograph. Shutter control 60 may be used to control a shutter positioned upstream relative to sample/blank 28 to selectively illuminate and limit exposure of sample/blank 28 while allowing light source 22 to stabilize before performing an experiment or measurement. Signals from computer 40 may be used to control monochromator 24 via associated excitation control 62 to control starting and ending scan wavelengths, wavelength increments, etc. In the embodiment illustrated in FIG. 2, auxiliary "A" channel 64 may be used to control optional components. Data channel 66 communicates data signals "I" associated with absorbance detector 30, and data channel 68 communicates data signals "R" associated with reference detector 26. Sample changer control 70 may optionally be provided to automate positioning of one or more samples within an associated sample chamber as illustrated and described in greater detail herein. Filter wheel control 72 may optionally be provided to automatically position an appropriate filter to reduce or eliminate undesired orders of light as the excitation scan proceeds through the desired range of excitation wavelengths. In the embodiment illustrated in FIG. 2, fluorescence detector data is provided via associated data channel 74 through electronics 52 and second port 42 to computer/processor 40 from a multichannel imaging CCD camera associated with a fluorescence spectrograph.

As generally illustrated in FIGS. 1 and 2, various embodiments of a system for analyzing a sample according to the present disclosure include an input light source 22, a multiple or multi-phase subtractive monochromator 24 positioned to receive light from input light source 22 and to sequentially illuminate sample (and/or blank) 28 with each of a plurality of wavelengths selected by monochromator 24. The system includes a multi-channel fluorescence detector 32 positioned to receive and substantially simultaneously detect multiple wavelengths of light emitted by the sample for each of the plurality of excitation wavelengths. Absorption detector 30 is positioned to receive and detect light passing through sample/blank 28. Computer 40 is in communication with monochromator 24, fluorescence detector 32, and absorption detector 30 via electronics 50, 52 and ports 42. Computer 40 includes control logic for controlling monochromator 24 to sequentially illuminate sample/blank 28 with each of the selected plurality of wavelengths while measuring absorption and fluorescence of sample/blank 28 based on signals received from the fluorescence and absorption detectors 32, 30, respectively. Reference detector 26 is in communication with computer 40 via electronics 50 and port 42 and cooperates with an associated beamsplitter (FIG. 3) positioned to direct a portion of light from monochromator 24 to reference detector 26. Computer 40 may adjust at least one of the absorption and fluorescence measurements based on a signal from reference detector 26.

Figure 3:
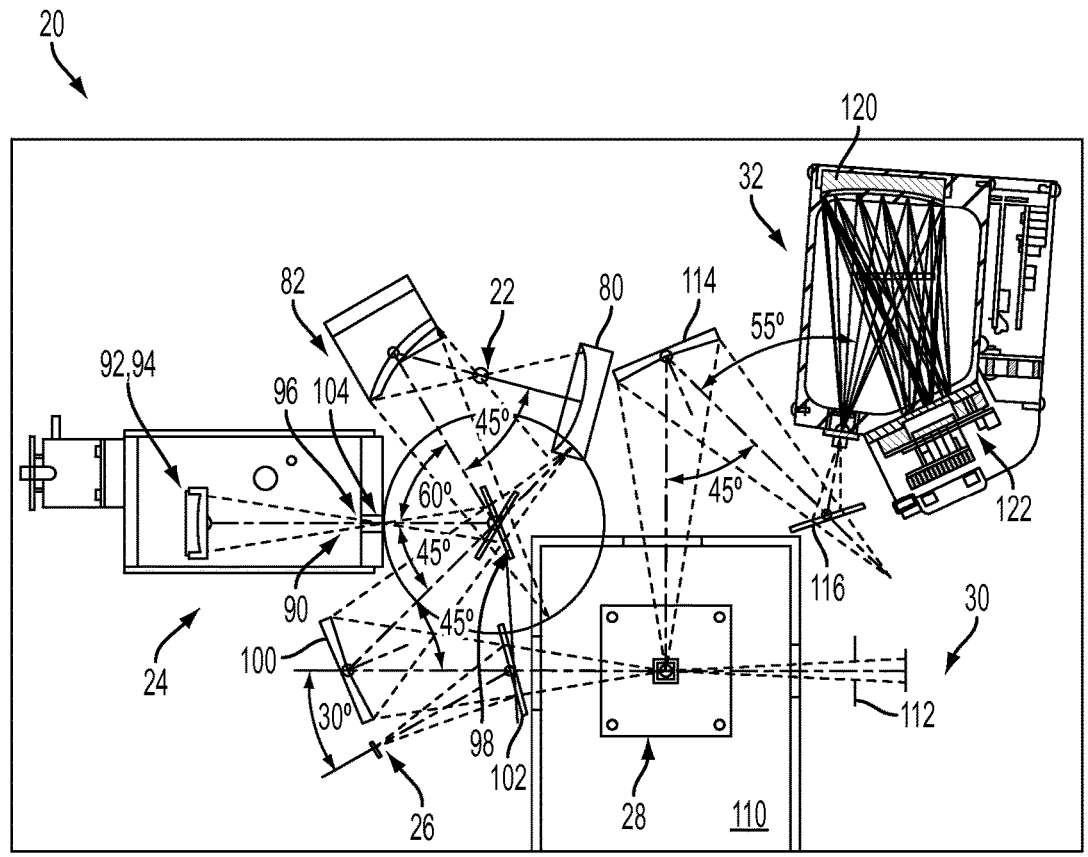
FIG. 3 is a schematic diagram illustrating operation of a system or method for analyzing a sample according to one embodiment of the present disclosure.
Figure 4:
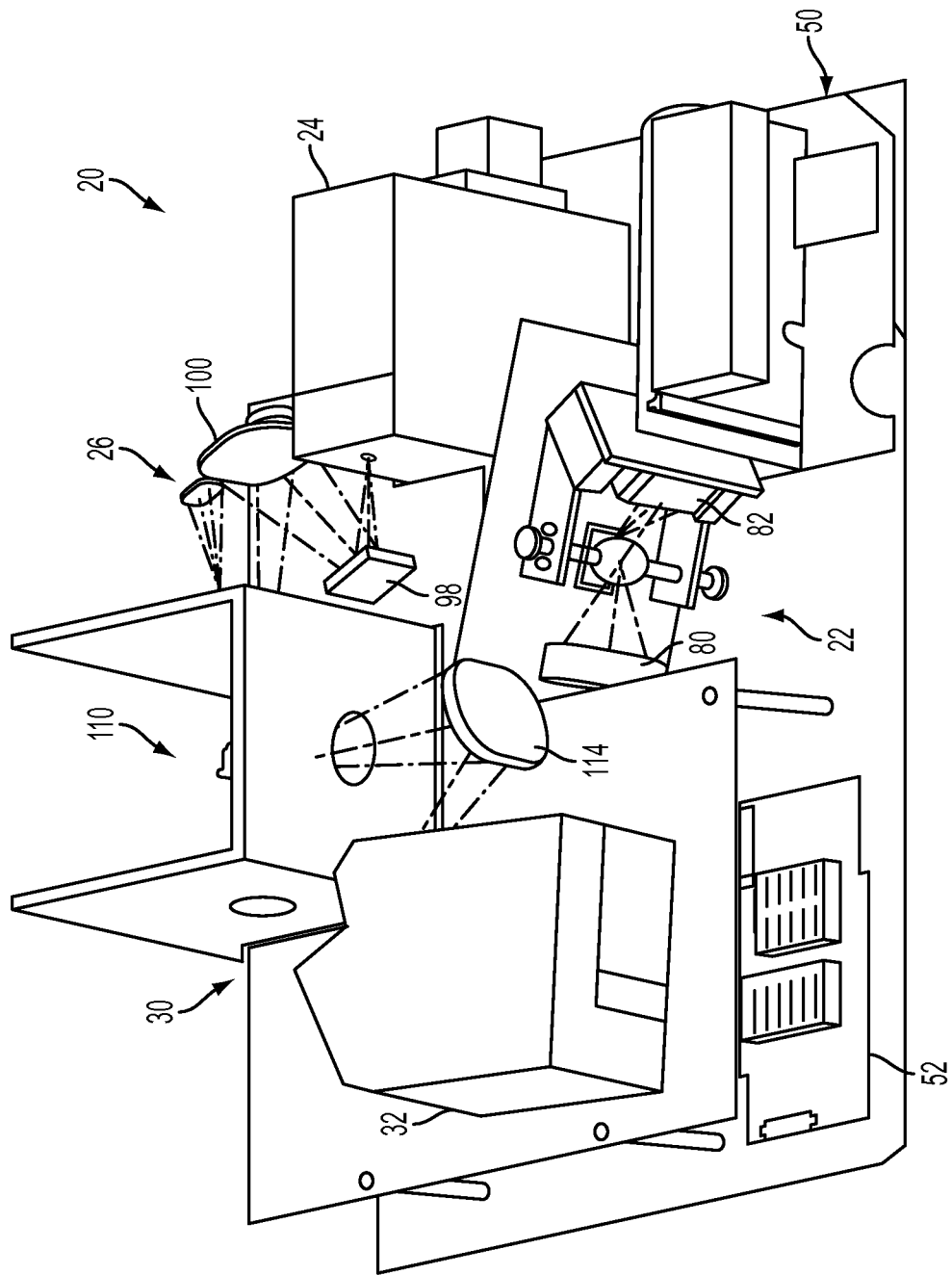
FIG. 4 is a perspective view of the embodiment illustrated in FIG. 1.

FIG. 3 is a schematic plan view and FIG. 4 is a perspective view illustrating component positioning for one embodiment of a system or method for analyzing a sample according to the present disclosure. System 20 includes an input light source 22 with one or more associated optical elements or components 80, 82 used to concentrate or gather light emitted by a bulb, tube or LED to improve the system efficiency. In the illustrated embodiment, light source 22 includes a concave mirror or reflector 80 and rear reflector 82 to direct light from the bulb in a desired output direction. Light from input source 22 is directed by reflector 82 to monochromator input mirror 84, which directs light to input 90 of double subtractive monochromator 24. Monochromator 24 includes first and second concave gratings 92, 94 which are generally vertically aligned (best shown in FIG. 5). Gratings 92, 94 are selectively positioned in response to a control signal to illuminate an output slit 96, which is generally vertically aligned with monochromator input 90, with diffracted light having a corresponding selected band of excitation wavelengths. A shutter 104 may be integrated into monochromator 24 or positioned at any convenient position within the instrument to control or limit illumination of sample 28 only during scanning measurements while allowing input light source 28 to reach a suitable operating temperature and stabilize.

At least one optical element is positioned to direct light from output 96 of monochromator 24 to sample 28. In the illustrated embodiment, a planar monochromator output mirror 98 directs diverging light from monochromator 24 to a concave or toroid mirror 100, characterized by an F/number of about F/3 in one embodiment. Converging light from toroid mirror 100 is directed to a beamsplitter 102 that is positioned to direct a first portion of the incident light from monochromator 24 toward a reference detector 26 and a second portion of the incident light to sample 28. Reference detector 26 may be implemented by a silicon photodiode, for example. Reference detector 26 may be positioned so that measurements may be used to normalize both absorption and fluorescence detectors.

Light passing through beamsplitter 102 enters sample chamber 110 and illuminates sample and/or blank 28 during a measurement scan. Light passing generally directly through sample 28 exits sample chamber 110 and passes through aperture 112 before illuminating absorption detector 30. In one embodiment, aperture 112 is sized to provide generally collimated light characterized by an F/number of about F/11 to absorption detector 30, which may be implemented by a single channel detector, such as a silicon photodiode. Use of slower optics for the absorption detector 30 enhances accuracy and linearity of absorbance detection. As such, various embodiments according to the present disclosure use faster excitation and fluorescence measurement optics than the absorbance measurement optics to provide higher light throughput for illumination of the sample and measurement of the relatively lower intensity light emitted by fluorescence while limiting light intensity of the light transmitted through the sample to the absorption detector to improve linearity and accuracy of the substantially simultaneous absorption measurement. Other embodiments may use a multichannel detector, such as a photodiode array (PDA), to obtain absorbance measurements. While this may reduce scanning time, it does not facilitate substantially simultaneous measurements to obtain a 3D spectrum. As described in greater detail herein, some embodiments may implement absorption detector 30 with a spectrograph to provide absorbance measurements.

Light emitted by sample 28 generally perpendicular to the excitation light passing through beamsplitter 102 exits sample chamber 110 through an associated aperture and is reflected by concave or toroid mirror 114 and planar mirror 116 to multichannel fluorescence detector 32. In the illustrated embodiment, multichannel fluorescence detector 32 is implemented by an imaging spectrograph having a concave grating 120 that diffracts input light to spread its component frequencies/wavelengths across cooled CCD detector 122. Use of a multichannel fluorescence detector 32 facilitates substantially simultaneous measurement of the fluorescence spectrum associated with each excitation wavelength of double subtractive monochromator 24 to significantly reduce measurement acquisition time relative to instruments that using a single channel scanning fluorescence detector.

Figure 5:
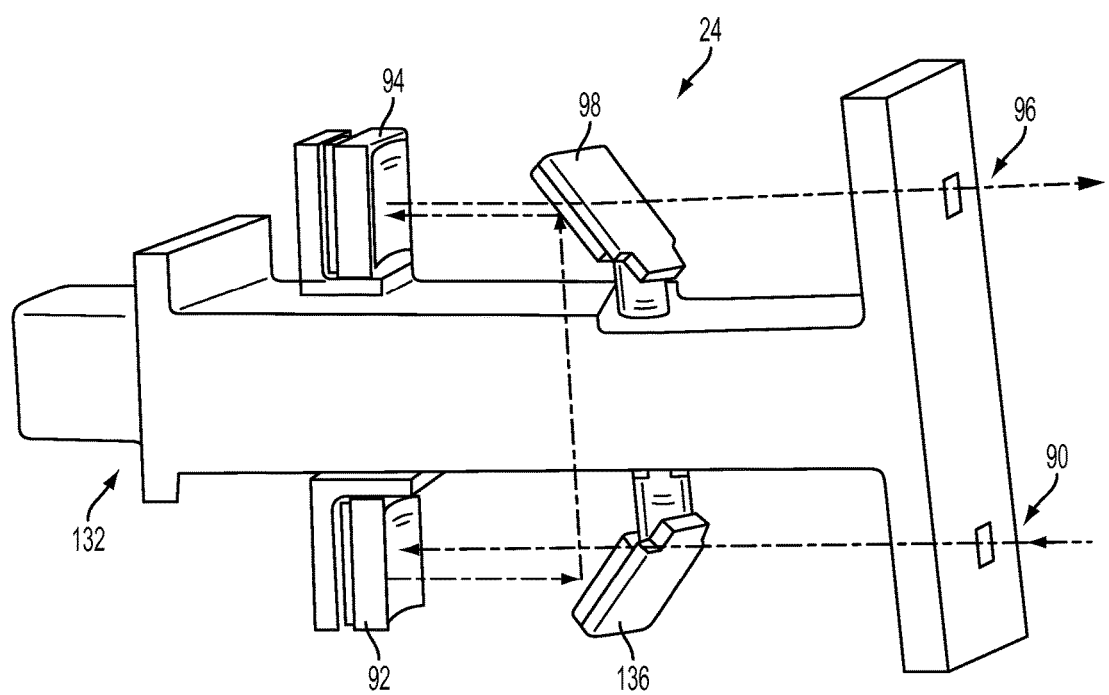
FIG. 5 is a perspective view of a subtractive double monochromator for use in a system or method for analyzing a sample according to various embodiments of the present disclosure.

FIG. 5 is a perspective view illustrating components of a double subtractive monochromator 24 for use in a system or method for analyzing a sample according to various embodiments of the present disclosure. Monochromator 24 includes first and second concave diffraction gratings 92, 94 selectively positioned to illuminate an output slit 96 with diffracted light having a corresponding selected band of excitation wavelengths. In operation, light from an input light source enters through input aperture 90 and is incident on a first concave diffraction grating 92. Diffracted light from grating 92 is reflected by first mirror 136 to second mirror 138 and to second grating 94 and to the exit 96. First and second concave diffraction gratings 92, 94 are arranged in a subtractive configuration such that the output of first concave diffraction grating 92 acts as the input to second concave diffraction grating 94 to produce near zero dispersion of the exiting excitation beam at exit 96 while reducing amplitude of stray light, i.e. light of non-selected wavelengths. Reducing stray light reduces or eliminates unwanted UV light (which is more susceptible to scattering) from illuminating the sample to reduce bleaching while also facilitating higher spectral resolution. Similarly, more accurate absorption measurements are possible as the spectra are randomly mixed.

Of course, various other monochromator configurations may be used to meet desired performance specifications for a particular application or implementation. For example, a monochromator configuration having one or more separate gratings/mirrors rather than an integrated concave grating may be used. Similarly, where dispersion performance is less important, a subtractive configuration may not be necessary. Likewise, more than two phases may be combined in a multiple monochromator to further reduce stray light and/or achieve various other performance requirements. In general, a multiple monochromator having at least two concave gratings arranged in a subtractive configuration may be used to provide desired stray light rejection and near zero dispersion suitable for a variety of applications.

Figure 6:
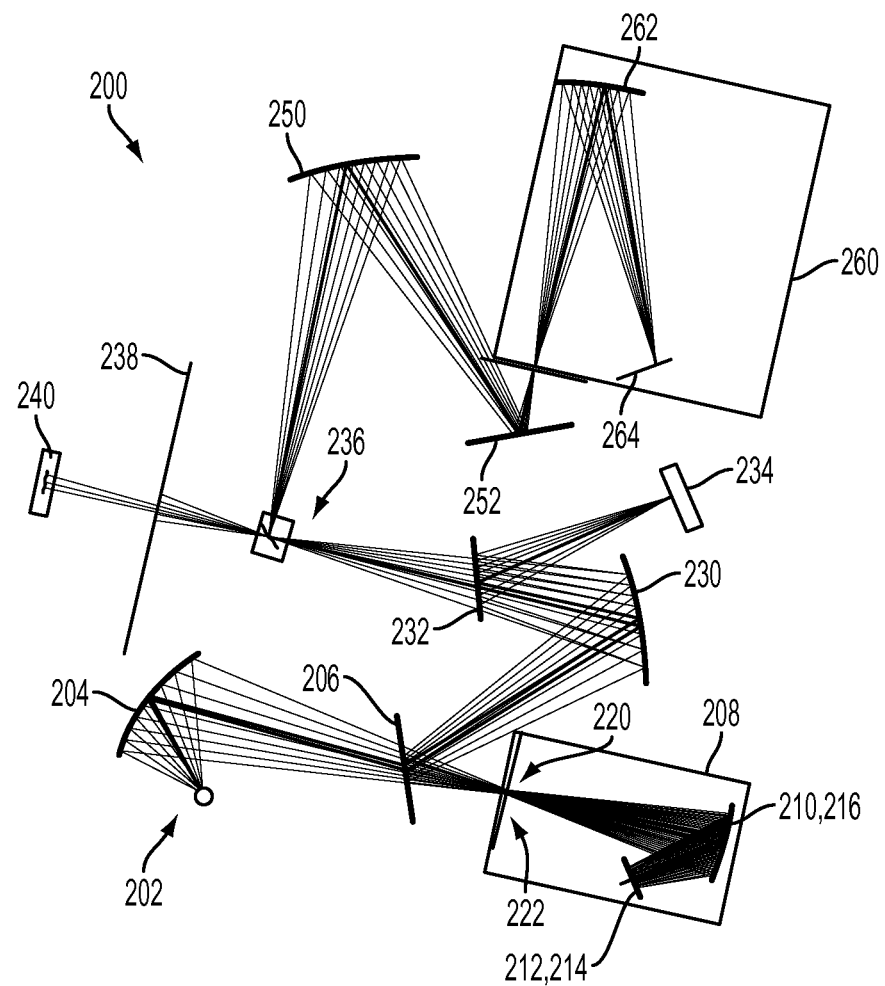
FIG. 6 is a schematic diagram illustrating operation of a system or method for analyzing a sample according to another embodiment of the present disclosure.

FIG. 6 is a simplified schematic illustrating another embodiment of a system or method for analyzing a sample according to the present disclosure. System 200 includes an input light source 202 with input light directed by elliptical reflector 204 toward double subtractive monochromator 208. Light from reflector 204 passes below or behind plane mirror 206 to an input aperture 220 of monochromator 208. Input light is diffracted by a first concave diffraction grating 210 to steering mirrors 212, 214 and a second concave diffraction grating 216 as previously described. Gratings 210, 216 may be selectively positioned to select a desired excitation wavelength with associated light exiting monochromator at the level of plane mirror 206 through an exit aperture 222. Plane mirror 206 directs the diverging excitation light of a selected wavelength to toroid mirror 230 having a numerical aperture corresponding to F/3. Toroid mirror 230 directs converging light to beamsplitter 232, which redirects a portion of the incident light to reference photodiode 234 while transmitting the remaining portion to sample 236. Light passing through sample 236 is incident on baffle 238 having an aperture to provide a numerical aperture corresponding to F/11 relative to absorption photodiode 240. Baffle/aperture 238 is operable to collimate light provided to absorption photodiode 240.

Any light emitted by sample 236 generally perpendicular to the excitation light is collected by a second toroid mirror 250 having a numerical aperture corresponding to F/3. Toroid mirror 250 redirects the generally diverging light in a converging beam toward the input of imaging spectrograph 260 via beam steering mirror 252. Imaging spectrograph includes an aberration correcting grating 262 that separates the input light into its component wavelengths for imaging on cooled CCD 264 so that multiple wavelength spectra can be collected for each of the plurality of excitation wavelengths supplied by double monochromator 208. Use of a cooled CCD detector 264 reduces dark noise and improves signal/noise ratio (SNR) to increase instrument sensitivity such that the instrument is suitable for a wide variety of applications, particularly those related to water quality analysis and associated CDOM measurements, for example.

Figure 7:
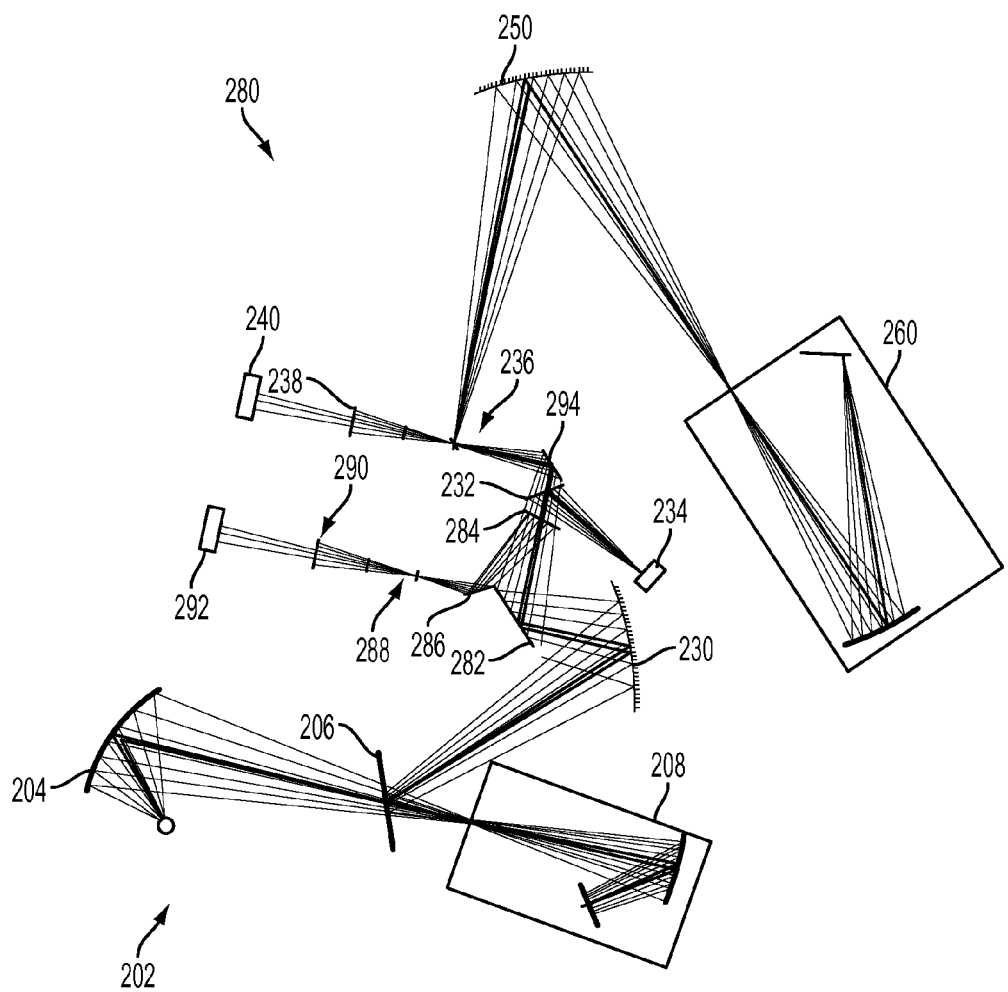
FIG. 7 is a schematic diagram illustrating operation of a system or method for analyzing a sample using a dual beam arrangement to illuminate a sample and blank with corresponding absorbance detectors according to various embodiments of the present disclosure.

FIG. 7 is a schematic diagram illustrating operation of a system or method for analyzing a sample using a dual beam arrangement to illuminate a sample and blank with a common excitation beam according to various embodiments of the present disclosure. System 280 includes an input light source 202, elliptical mirror 204, flat or plane mirror 206 and double monochromator 208 similar to the arrangement illustrated in FIG. 6. Likewise, excitation light from monochromator 208 is directed to toroid mirror 230. An additional beam steering mirror 282 is positioned to redirect the excitation beam to a removable beamsplitter 284, which creates a dual excitation beam by reflecting a portion of the light to steering mirror 286 and through a blank 288. Light passing through blank 288 is incident on a baffle/aperture 290 with generally collimated light passing through to an associated blank absorbance detector 292.

A portion of light that passes through removable beamsplitter 284 is redirected by beamsplitter 232 to reference photodiode 234 as previously described. Light transmitted by beamsplitter 232 is redirected by steering mirror 294 through sample 236. Light passing through sample 236 is incident on baffle/aperture 238 with a portion of the light falling on absorbance photodiode 240.

With the dual beam arrangement illustrated in FIG. 7, absorbance measurements can be substantially simultaneously collected for blank 288 and sample 238. Removable beamsplitter 284 may be manually or automatically removed or repositioned during fluorescence measurements of sample 236 to provide increased excitation beam intensity to improve sensitivity of fluorescence measurements for sample 236. Similar to previously described embodiments, light emitted by sample 236 generally perpendicular to the excitation beam is directed by a toroid mirror 250 to a multichannel fluorescence detector 260, which may be implemented by an imaging spectrograph having a cooled CCD to provide desired instrument characteristics as previously described.

Figure 8:
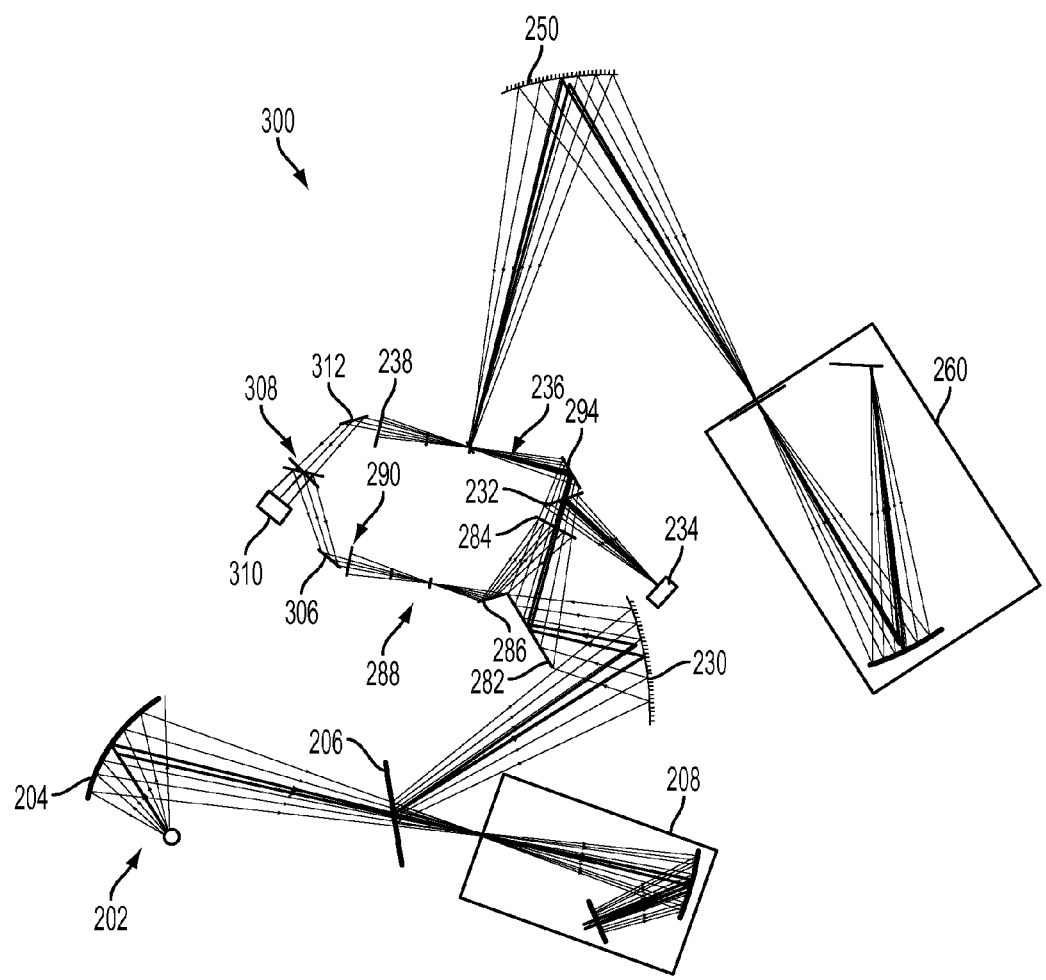
FIG. 8 is a schematic diagram illustrating operation of a system or method for analyzing a sample using a dual beam arrangement to illuminate a sample and blank with a single absorbance detector and associated chopper according to various embodiments of the present disclosure.

FIG. 8 is a schematic diagram illustrating operation of a system or method for analyzing a sample using a dual beam arrangement to illuminate a sample and blank with a single absorbance detector and associated chopper according to various embodiments of the present disclosure. The arrangement of FIG. 8 is similar to the arrangement of FIG. 7 with respect to the structure and function of like numbered elements. However, in the embodiment of FIG. 8, light from blank 288 passing through baffle/aperture 290 is redirected by mirror 306 to chopper 308. Similarly, light from sample 236 passing through baffle/aperture 238 is redirected by mirror 312 to chopper 308. Chopper 308 selectively directs light from either blank 288, or light from sample 236 to absorbance detector 310, so that a single absorbance detector can be used for absorbance measurements of both blank 288 and sample 236. Chopper 308 may be controlled so that corresponding measurements from blank 288 and sample 232 are acquired sequentially but nearly simultaneously.

Figure 9:
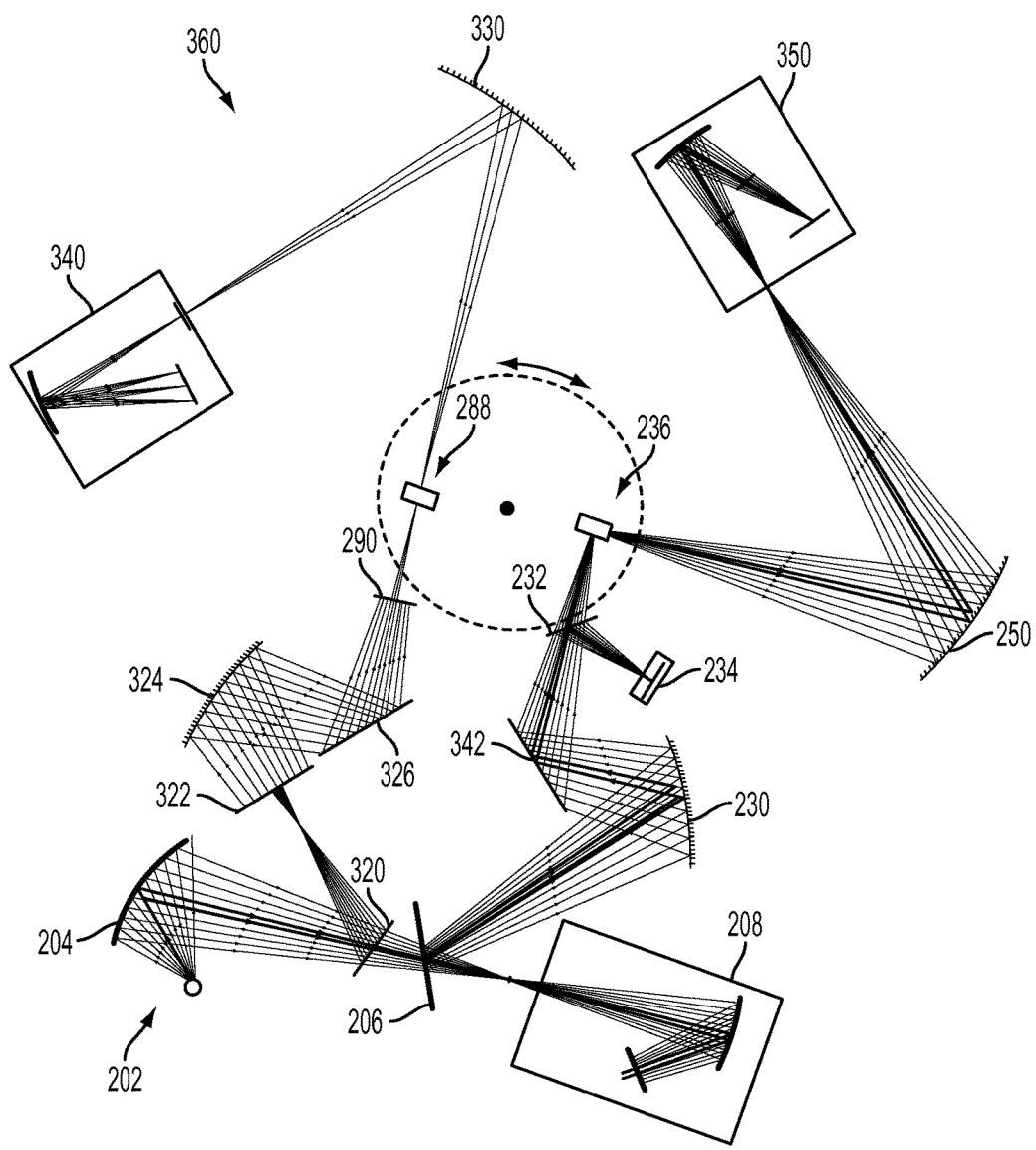
FIG. 9 is a schematic diagram illustrating operation of a system or method for analyzing a sample using direct illumination in the absorption path and a spectrograph for absorbance detection according to various embodiments of the present disclosure.

FIG. 9 is a schematic diagram illustrating operation of a system or method for analyzing a sample using direct illumination in the absorption path and a spectrograph for absorbance detection according to various embodiments of the present disclosure. System 360 includes various components with structure and function as previously described with respect to like numbered elements. In the embodiment of FIG. 9, a portion of light from input light source 202 is used to directly illuminate blank 288 for absorbance measurement. Beam splitter 320 redirects a portion of light from light source 202 through element 322. Toroid mirror 324 forms a converging beam that is redirected by steering mirror 326 and passes through baffle/aperture 290 before illuminating blank 288. Light passing through blank 288 is reflected by toroid mirror 330 toward absorbance detector 340, implemented by a spectrograph in this embodiment.

Fluorescence measurements are acquired from light emitted from sample 236 at a right angle relative to the excitation beam using spectrograph 350. Light of a selected wavelength exits double monochromator 208 and is redirected by plane mirror 206, toroid mirror 230 and plane mirror 342 through beam splitter or window 232 to sample 236. As previously described window or beamsplitter 232 directs a portion of the incident light to reference photodiode 234. Light emitted from sample 236 is collected by toroid mirror 250 and redirected to spectrograph 360. In this embodiment, the sample compartment is configured to rotate to alternate the sample cell 236 and blank cell 288.

Figure 10:
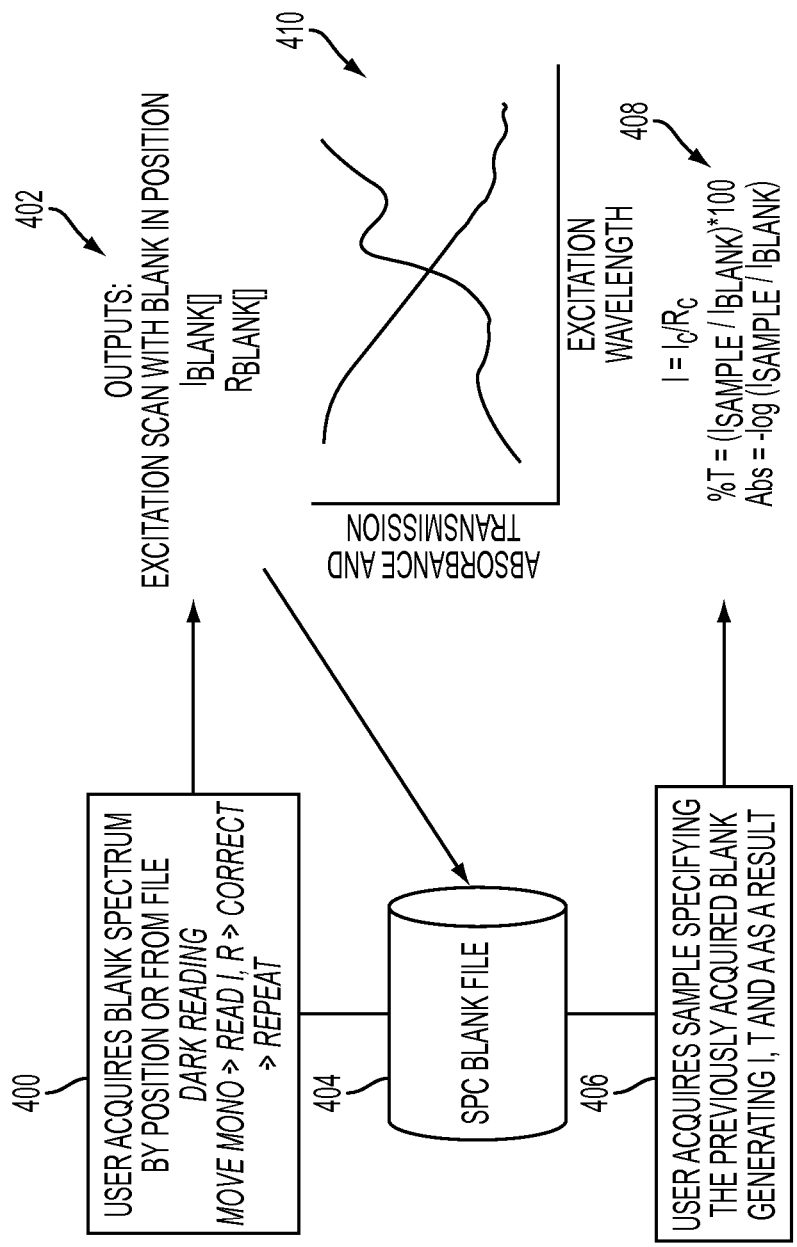
FIG. 10 illustrates a representative absorbance measurement for a system or method for analyzing a sample according to various embodiments of the present disclosure.

FIG. 10 illustrates a representative absorbance measurement for a system or method for analyzing a sample according to various embodiments of the present disclosure. As previously described, various embodiments include a computer (FIG. 2) in communication with the double subtractive monochromator, multi-channel fluorescence detector, absorption detector, and reference detector to control the excitation scanning and resulting data acquisition for subsequent analysis. As generally illustrated in FIG. 10, the computer may include control logic implemented in software and/or hardware to perform an absorbance measurement of a blank and sample. Block 400 represents acquiring an absorbance spectrum for a blank by positioning the blank within the measurement chamber and performing a series of measurements that may include a baseline dark reading with the shutter closed and no excitation light illuminating the blank. The measurement proceeds by controlling the monochromator to provide a first selected wavelength with the computer storing the associated "I" data from the absorbance detector and "R" data from the reference detector. The computer may correct or normalize the absorbance data using the reference data. This process is repeated for each wavelength increment until the desired ending wavelength is reached. The output of the excitation scan with the blank in the measurement position as represented by block 402 may be stored for subsequent measurements as represented at 404.

For blanks with previously stored data, the user may retrieve the corresponding data file as represented at block 400 rather than performing a new excitation scan. Measurement of a sample may then be completed as represented by block 406. The sample is placed into position within the measurement chamber with a corresponding blank file specified. Measurement proceeds in a similar fashion for each wavelength selected by the monochromator with the resulting data acquired from the absorbance detector and reference detector and corrected or normalized as indicated at 408, i.e. $I=I_c/R_c$. Transmission (T) is calculated according to: $\% \, T=(I_{sample}/I_{blank})*100$ and absorbance is calculated according to: $Abs=-\log(I_{sample}/I_{blank})$. The results may be plotted as a function of excitation wavelength as indicated at 410, for example. Of course, various other data acquisition and analysis techniques may be used depending on the particular application and implementation.

Figure 11A:
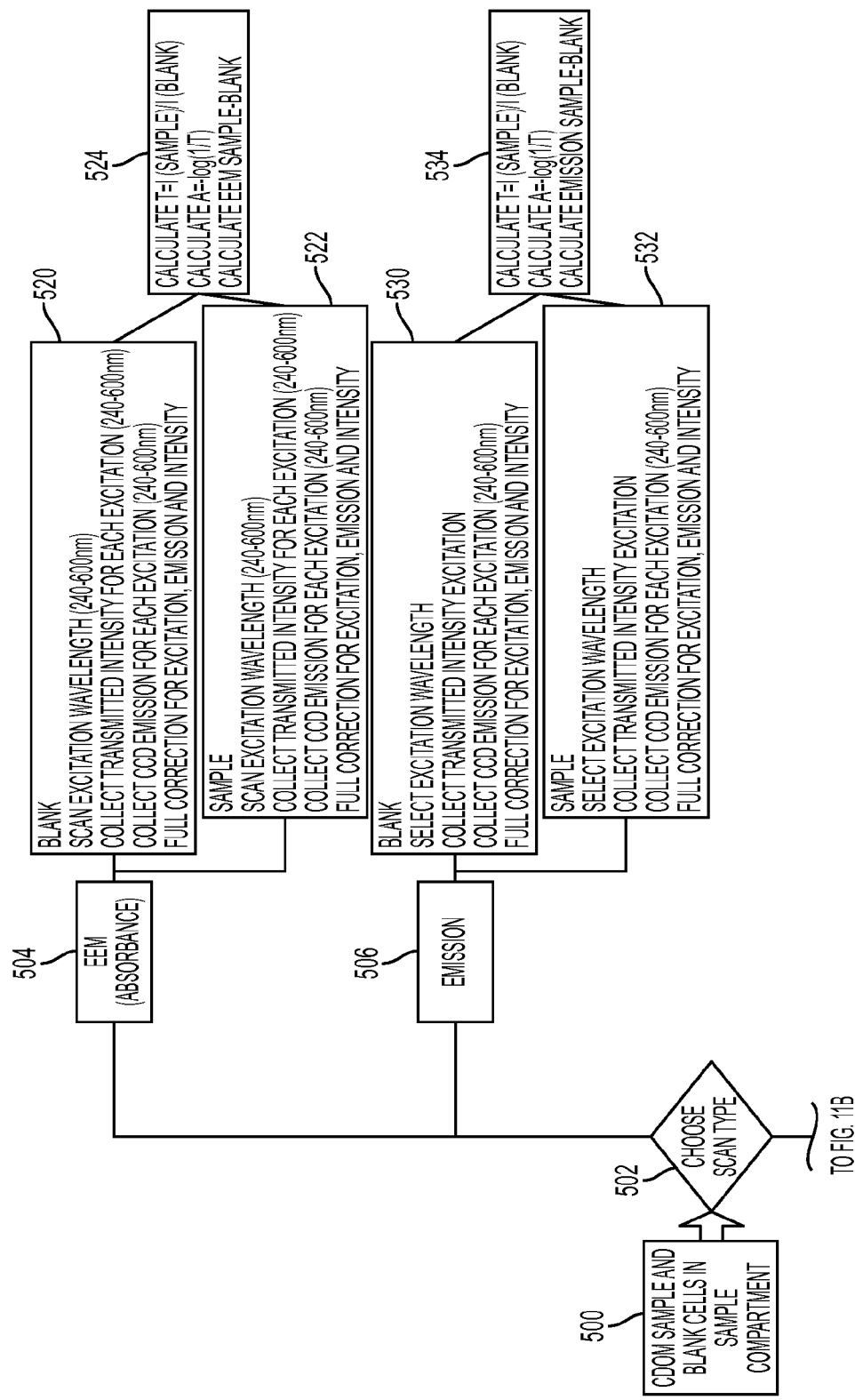
FIGS. 11A and 11B illustrate selectable operating modes for obtaining representative absorbance and fluorescence measurements in a system or method for analyzing a sample according to embodiments of the present disclosure.
Figure 11B:
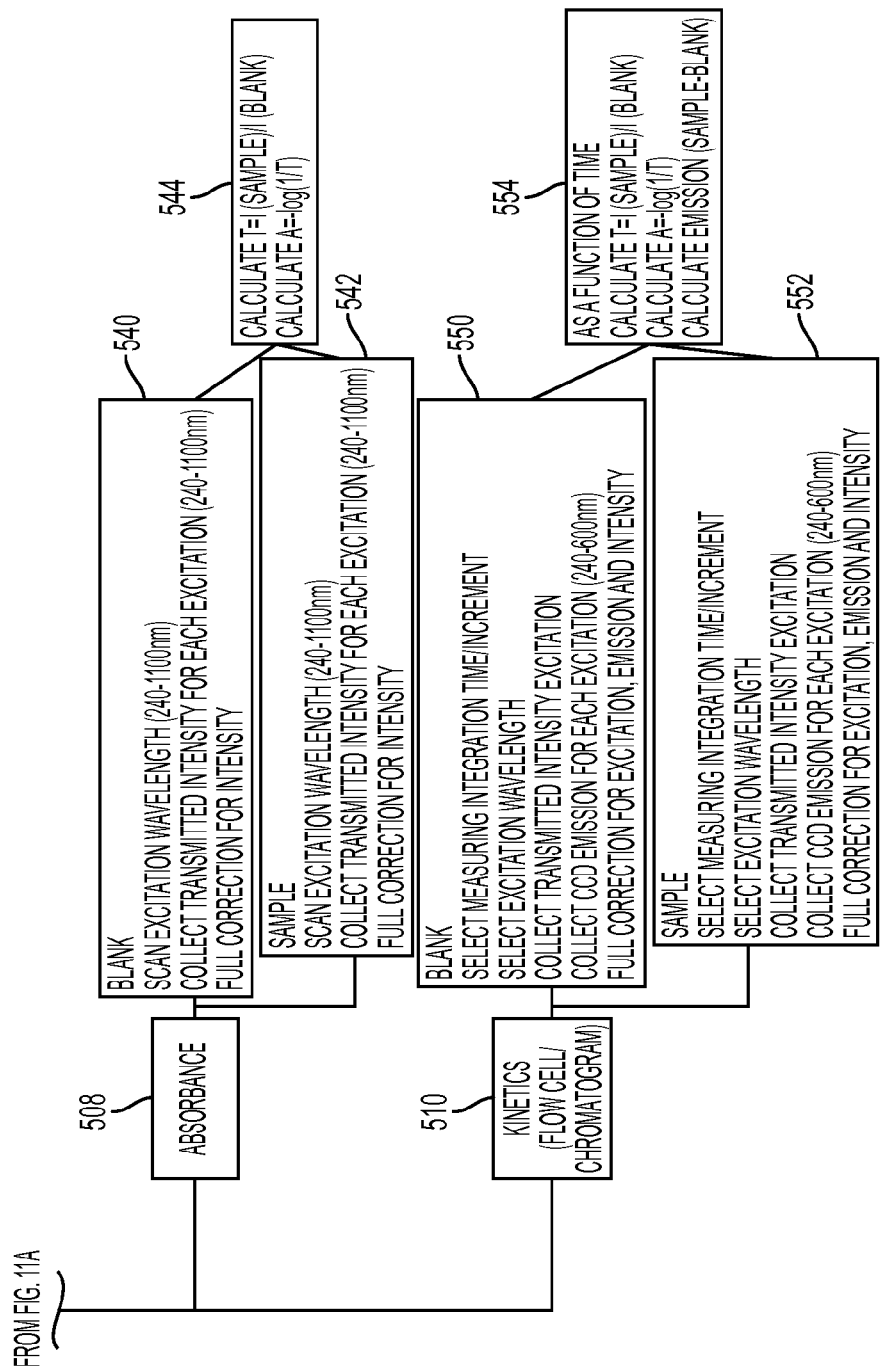

FIGS. 11A and 11B illustrate selectable operating modes for obtaining representative absorbance and fluorescence measurements in a system or method for analyzing a sample according to embodiments of the present disclosure. As previously described, various embodiments according to the present disclosure include features particularly suited for water quality analysis and quantitation of CDOM. For example, in this embodiment, the sample compartment is configured to rotate to alternate the sample cell and blank cell as illustrated and described above with reference to FIG. 9. As such, the following representative operating modes are described with respect to a water quality analysis application. Similar modes or measurements may be performed for other applications.

A CDOM sample cell and blank cell are positioned in the sample compartment as represented by block 500. The user then selects a scan type as represented by block 502. In the illustrated embodiment, operating modes or scan types include an EEM (absorbance) measurement 504, emission (fluorescence) measurement 506, absorbance measurement 508, and kinetics (flow cell/chromatogram) analysis as represented by block 510. EEM (absorbance) measurement 504 proceeds in a similar fashion for a blank 520 and sample 522. As previously described, data associated with a particular blank may be obtained from a previously stored file if available. Otherwise, the blank measurement data is obtained by illuminating the blank with a plurality of excitation wavelengths between 240 nm and 600 nm in this example. Transmitted intensity data for each excitation wavelength is determined using the absorbance detector and reference detector signals as previously described. Emission spectra data as measured by the multi-channel CCD fluorescence detector is collected for each excitation wavelength. The data is then corrected for excitation, emission, and intensity. In one embodiment, the data is corrected to eliminate inner filter effects as described in greater detail below. Data from the blank and sample are used to calculate the transmission (T), Absorbance (A), and EEM as represented by block 524. This software enables the user to select a desired method for automatically analyzing the data and displaying the measured and analyzed data to reduce acquisition time and reduce or eliminate manual data analysis for the user.

Selection of the emission measurement 506 proceeds in a similar fashion as the EEM measurement 504 with data collected for a blank as represented by block 530. However, rather than automatically sequentially scanning from a starting to an ending wavelength, a single excitation wavelength is selected as indicated in block 530. Likewise, a single excitation wavelength is selected for the sample as indicated in block 532. The corrected blank and sample data are then used to determine the transmission (T), absorbance (A), and EEM as represented by block 534 to reduce or eliminate inner filter effects.

As also illustrated in FIG. 11, selection of an absorbance measurement 508 proceeds in a similar fashion as the EEM measurement 504 with data collected for a blank as represented by block 540 and a sample as represented by block 542. As illustrated in block 540, the excitation wavelength is scanned from a selected starting wavelength to a selected ending wavelength, such as from 1100 nm to 240 nm in this example. For each excitation wavelength, the transmitted intensity is collected based on the absorption detector signals and corrected for the intensity based on at least one corresponding reference detector signal. The blank and sample data are then used to calculate transmission (T) and absorbance (A) as represented by block 544.

Instruments equipped with a flow cell may perform a kinetics analysis as represented by block 510 with similar measurements collected for a blank as represented by block 550 and a sample as represented by block 552. A measuring integration time and increment are selected in addition to an excitation wavelength. Transmitted intensity data is then collected for the selected excitation wavelength. Emission spectra data (multiple wavelengths) is also collected from the multi-channel fluorescence detector and the data is corrected for excitation, emission, and intensity to eliminate inner filter effect. Blank data and sample data are then used to plot transmission (T), absorbance (A) and emission data as a function of time as represented by block 554.

Embodiments according to the present disclosure provide a benchtop analytical research instrument that coordinates fluorescence excitation-emission mapping (EEM) and absorbance analysis that is particularly suited for water quality analysis of suspended and dissolved organic and inorganic materials, but also suitable for food science and other applications requiring EEM's and absorbance assays with facilitated qualitative and quantitative analyses. In addition to the measurements/calculations described above, various embodiments provide the ability to transfer data in/out of a number of commercially available multivariate analysis packages such as MatLab and Eigenvector to facilitate parallel factor analysis (PARAFAC), sometimes referred to as canonical decomposition, principle component analysis (PCA), and the like.

Figure 12:
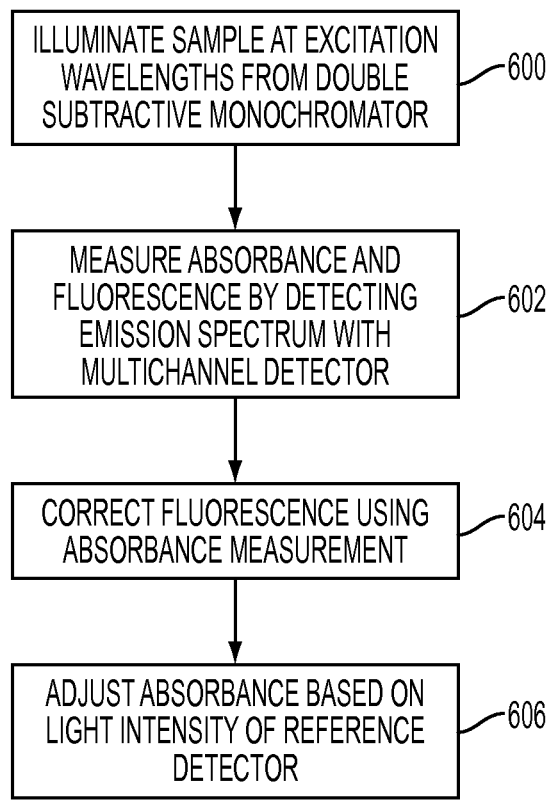
FIG. 12 is a flowchart illustrating operation of a system or method for analyzing a sample according to embodiments of the present disclosure.

FIG. 12 is a flowchart illustrating operation of a system or method for analyzing a sample according to embodiments of the present disclosure. The system or method include sequentially illuminating a sample and/or blank at a plurality of excitation wavelengths emitted by a double subtractive monochromator as represented by block 600. The system or method also include measuring absorbance by the sample/blank by detecting light passing through the sample and fluorescence of the sample by detecting an emission spectrum of light emitted by the sample for each excitation wavelength using a multichannel detector as represented by block 602. The absorbance and fluorescence may be measured using the same or a common excitation beam such that both measurements may be acquired substantially simultaneously. The system and method may also include correcting the fluorescence measurement using the absorbance measurement as represented by block 604. For example, in one embodiment, the following equation may be used:

$$F_{ideal} = F_{observed} * \exp((OD_{ex} + OD_{em})/2)$$

Where $F_{ideal}$ represents the ideal fluorescence signal spectrum expected in the absence of inner filter effects, $F_{observed}$ represents the observed fluorescences, $OD_{ex}$ and $OD_{em}$ represent the measured absorbance values at the respective excitation and emission wavelength coordinates of the EEM. In addition, the system or method may include adjusting the absorbance measurement based on light intensity detected by a reference detector positioned to receive a portion of light from the monochromator as represented by block 606.

As illustrated by the previously described representative embodiments, systems and methods for sample analysis according to the present disclosure provide simultaneous measurement of absorption and fluorescence to facilitate qualitative and quantitative analysis of dissolved and/or suspended organic and inorganic substances in water samples with desired speed, accuracy and precision. Simultaneous acquisition of absorbance and fluorescence data in a single instrument reduces or eliminates inaccurate correlations associated with time-dependent optical and chemical changes in the samples between measurements. Furthermore, simultaneously acquired absorbance data can be used to correlate and correct fluorescence spectral information, in addition to providing a wealth of independent data on dissolved and suspended organic and inorganic compounds. Automatic filtering of the excitation and emission beams eliminates grating order artifacts.

Systems and methods incorporating a multiple grating excitation monochromator provide excellent stray light rejection for Rayleigh scattering and grating orders with deep UV sensitivity. Use of a reference diode for excitation monitoring and correction provides traceable optical correction of fluorescence excitation spectra and compensates for any input lamp drift. Use of a modular sample compartment that accommodates sample, blank and flow cells facilitates blank correction (subtraction) and flow for autosampling and online monitoring while reducing or eliminating contamination. High-speed optics for fluorescence measurements improves throughput for fluorescence sensitivity and SNR for water Raman scattering. Use of a cooled CCD as an imaging detector for the fluorescence emission spectrometer provides rapid data acquisition with high UV-VIS detection sensitivity and low dark noise. Simultaneous absorption measurements facilitate better correction for reabsorbed fluorescence signals resulting from inner filter effects within the sample than the absorbance measurement implemented by various prior art instruments. Similarly, appropriately apertured absorption optics provide a collimated beam for improved linearity and accuracy and facilitate use of a low-cost silicon photodiode detector.

While exemplary embodiments are described above, it is not intended that these embodiments describe all possible forms of a system or method for analyzing a sample according to the present disclosure. Rather, the words used in the specification are words of description rather than limitation, and it is understood that various changes may be made without departing from the spirit and scope of the disclosure. As previously described, the features of various representative embodiments may be combined in ways that are not explicitly illustrated or described to form further embodiments. While various embodiments may have been described as providing advantages or being preferred over other embodiments with respect to one or more desired characteristics, as one of ordinary skill in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, operation, etc. Any embodiments described herein as less desirable than other embodiments or prior art implementations with respect to one or more characteristics are not outside the scope of the disclosure and may be desirable for particular applications.

What is claimed is:

1. A method for analyzing a sample, the method comprising:
    illuminating the sample at a plurality of excitation wavelengths using an excitation monochromator configured to generate an excitation beam;
    measuring absorbance by the sample by detecting light from the excitation beam passing through the sample;
    adjusting detected absorbance based on light intensity detected by a reference detector positioned to receive a portion of the excitation beam from the monochromator;
    measuring fluorescence of the sample by detecting an emission spectrum of light emitted by the sample perpendicular to the excitation beam illuminating the sample for each excitation wavelength based on a signal generated by an associated detector; and
    correcting the fluorescence measurement using the adjusted detected absorbance.

2. The method of claim 1 wherein illuminating comprises: illuminating the sample using a double subtractive monochromator.

3. The method of claim 1 wherein measuring fluorescence comprises measuring fluorescence of the sample based on a signal generated by an associated multi-channel detector.

4. The method of claim 1 wherein measuring fluorescence comprises measuring fluorescence of the sample based on a signal generated by an imaging detector.

5. The method of claim 1 wherein the sample is contained within a cuvette.

6. The method of claim 1 wherein adjusting detected absorbance comprises adjusting detected absorbance based on light intensity detected by a photodiode.

7. The method of claim 1 wherein adjusting detected absorbance comprises adjusting detected absorbance based on light intensity detected by a photomultiplier tube (PMT).

8. The method of claim 1 wherein measuring fluorescence of the sample comprises measuring fluorescence based on a signal generated by a scanning monochromator.

9. A system for analyzing a sample comprising:
    an input light source;
    a reference detector;
    an excitation monochromator positioned to receive light from the input light source and to sequentially illuminate the sample with an excitation beam for each of a plurality of wavelengths;
    a beamsplitter positioned to direct a portion of light from the excitation beam to the reference detector;
    a multi-channel fluorescence detector positioned to receive and detect multiple wavelengths of light emitted by the sample perpendicular to the excitation beam illuminating the sample for each of the plurality of excitation wavelengths;
    an absorption detector positioned to receive and detect a portion of the excitation beam passing through the sample;
    and
    a computer in communication with the excitation monochromator, the reference detector, the fluorescence detector, and the absorption detector, the computer controlling the excitation monochromator to sequentially illuminate the sample with each of the plurality of wavelengths while measuring absorption and fluorescence of the sample based on signals received from the fluorescence detector and the absorption detector, the computer configured to trigger the fluorescence detector, and the absorption detector, and to correct a fluorescence measurement of the sample by an absorbance measurement obtained simultaneously with the fluorescence measurement, wherein the absorbance measurement is adjusted using a signal from the reference detector.

10. The system of claim 9 wherein the absorption detector comprises at least one photodiode.

11. The system of claim 9 wherein the fluorescence detector comprises a scanning monochromator.

12. The system of claim 9 wherein the fluorescence detector comprises an imaging detector.

13. A system for analyzing a sample, the system comprising:
    an excitation light source positioned to output an excitation beam having selected bands of excitation wavelengths;
    at least one optical element positioned to direct light at least a portion of the excitation beam from the excitation light source toward a sample;
    a reference detector;
    a beamsplitter positioned to direct a first portion of the excitation beam from the at least one optical element to the reference detector and a second portion of the excitation beam from the at least one optical element to the sample;
    an absorption detector positioned to receive a portion of the excitation beam transmitted through the sample;
    a multi-channel fluorescence detector positioned to detect multiple orders of diffracted light emitted by the sample perpendicular to the excitation beam illuminating the sample for each band of excitation wavelengths; and
    a processor in communication with the excitation light source, the reference detector, the absorption detector, and the fluorescence detector to simultaneously detect absorbance and fluorescence of the sample for each of the selected bands of excitation wavelengths.

14. The system of claim 13 wherein the reference detector comprises a photodiode.

15. The system of claim 13 wherein the at least one optical element comprises a concave mirror.

16. The system of claim 13 wherein the at least one optical element comprises a lens.

17. The system of claim 13 wherein the reference detector comprises a photomultiplier tube (PMT).

* * * * *

UNITED STATES PATENT AND TRADEMARK OFFICE
CERTIFICATE OF CORRECTION

PATENT NO.         : 10,168,310 B2
APPLICATION NO.    : 14/556976
DATED              : January 1, 2019
INVENTOR(S)        : Adam Matthew Gilmore et al.

Page 1 of 1

It is certified that error appears in the above-identified patent and that said Letters Patent is hereby corrected as shown below:

In the Claims

Column 16, Line 28, Claim 13:
After "at least one optical element positioned to direct"
Delete "light".

Signed and Sealed this
Twenty-third Day of April, 2019

Andrei Iancu
*Director of the United States Patent and Trademark Office*